(12) United States Patent
Falsetti et al.

(10) Patent No.: US 7,757,364 B2
(45) Date of Patent: Jul. 20, 2010

(54) METHODS FOR MODIFYING FINISHED MACHINE COMPONENT FORGINGS FOR ULTRASONIC INSPECTION COVERAGE

(75) Inventors: Robert V. Falsetti, Schenectady, NY (US); Francis Alexander Reed, Princetown, NY (US); Robert Bergman, Scotia, NY (US)

(73) Assignee: General Electric Company, Schenectady, NY (US)

( * ) Notice: Subject to any disclaimer, the term of this patent is extended or adjusted under 35 U.S.C. 154(b) by 1015 days.

(21) Appl. No.: 11/463,432

(22) Filed: Aug. 9, 2006

(65) Prior Publication Data

US 2008/0047122 A1    Feb. 28, 2008

(51) Int. Cl.
*B23Q 17/00* (2006.01)
(52) U.S. Cl. ................................. 29/407.01
(58) Field of Classification Search ............ 29/407.01, 29/407.04, 407.05, 407.09, 527.4; 700/90; 702/35, 36, 39, 104; 73/622, 593, 599, 602, 73/600, 628, 641, 597; 364/507, 550, 480, 364/492, 146
See application file for complete search history.

(56) References Cited

U.S. PATENT DOCUMENTS

| 5,963,882 A * | 10/1999 | Viertl et al. ................. 702/39 |
| 7,017,414 B2 * | 3/2006 | Falsetti et al. ............... 73/600 |
| 7,650,790 B2 * | 1/2010 | Wright ....................... 73/622 |

* cited by examiner

*Primary Examiner*—John C Hong
(74) *Attorney, Agent, or Firm*—Sutherland Asbill & Brennan LLP

(57) ABSTRACT

To achieve improved ultrasonic testing coverage of a finished machined component, the present invention applies a method for modifying a finished machine component forging for ultrasonic inspection. A forging envelope may be constructed in the shape of a right circular cylinder that surrounds a machine component forging. Then material may be added to the forging envelope in the direction of the forging equal to about 2 times a wavelength of an ultrasonic inspection device. Additional material may then be added to an inspection surface of the forging envelope equal to the dimension of a transducer dead zone, if the forging cannot be inspected ultrasonically from two opposing surfaces in the forged direction. Lastly, material may be added to the forging envelope in a direction perpendicular to the forging direction equal to a transducer footprint plus the break edge radius.

5 Claims, 4 Drawing Sheets ated of the dead zones due to resolution of the smaller defect
response from the larger back wall echo.

Therefore, a need exists for a system and method for determining the proper application of extra material to the forging envelope to create a geometric shaping for the forging necessary to achieve improved ultrasonic inspection coverage.

METHODS FOR MODIFYING FINISHED MACHINE COMPONENT FORGINGS FOR ULTRASONIC INSPECTION COVERAGE

FIELD OF THE INVENTION

This invention relates generally to the creation of a forging envelope to form machined components which allow for ultrasonic inspection coverage to detect defects in the finished component.

DESCRIPTION OF THE RELATED ART

Designing forgings requires that the forging envelope be constructed such that all of the volume of the finished machine component that will be machined from the forging receives an ultrasonic inspection in the proper direction and at the specified sensitivity to ensure internal defects that may be introduced during the ingot melting, forging and heat treatment processes are detected. Extra material must be added to the finished machine component shape to construct a forging shape that takes into account the various transducer dead zones and geometric boundary reflections that preclude defect detection by ultrasonic testing.

In currently existing systems, extra material is typically added to forgings to allow for machining tolerances and handling blemishes that may occur. Forgings made for the aerospace industry are inspected using immersion ultrasonic testing methods that lessen the transducer dead zone by pulsing the transducer in water. The water acts to deplete the transducer dead zone prior to sound entering the forging. However, there still remains a large interface reflection that can prevent detection of defects near the surface of the forging. In prior art systems, it is common for the design of a forging to include sufficient material to allow this large signal response to die down prior to sound entering the finished machine part. These forgings are typically tested using high transducer oscillation frequencies and focused beams that lessen the dead zone due to the water-to-metal interface.

However, these immersion techniques are not useful for larger scale forgings. For example, in prior art systems, large forgings designed for power generation applications are typically inspected by a contact ultrasonic method, where the transducer is directly coupled to the forging. This is due to the heavier weight and dimensions of the forgings which would require much larger immersion tanks and part manipulating equipment that would not be cost effective. Lower transducer oscillation frequencies and unfocused probes are commonly used because the size of the forgings requires a higher sound transmission energy into the forging to compensate for increased attenuation and scanning of large parts in an acceptable time frame.

Another problem with existing systems, is that when steps are included in the forging envelope to reduce the weight and cost of the forging, these steps can interfere with the ultrasonic test and introduce regions that are not inspected. On disc shaped forgings forged in the axial direction, proper alignment of the steps on each side of the forging is required such that fewer areas are missed by the ultrasonic test. On long cylindrical forgings that are forged in the radial direction, the steps may be re-machined between ultrasonic tests to obtain improved inspection coverage.

Problematically, the amount of extra stock that must be added due to steps in the forging envelope is neglected and small defects are not separated from the large back wall reflection for disc shaped forgings forged and tested in the axial direction. These forgings are also sometimes tested in both opposing axial directions without sufficient consider-

BRIEF DESCRIPTION OF THE INVENTION

The present invention fulfills these above-listed needs through a system and method which can improve forging shape design to achieve improved ultrasonic inspection coverage. The invention's method of doing this provides for much greater inspection coverage than prior art methods and provides for more accurate results from the inspections.

Many types of defects can be created during the melting and the forging process. These may include melt related inclusions and chemical segregation, forging bursts and laps, heat treatment quench cracks, etc. Melt related defects tend to align themselves with the material flow lines during the forging process, whereas forging defects tend to be multidirectional. For ultrasonic testing to be most effective, the direction of the sound beam should be perpendicular to the defect orientation. Furthermore, the centerline of the ultrasonic transducer is positioned on the forging envelope such that the entire volume of the finished machined part is scanned in the principal direction by the maximum energy point in the ultrasonic beam along the axis of the transducer. Addition of extra material to construct the forging envelope must take into consideration the forging process and material flow lines so that the ultrasonic test is performed in the most effective direction for defect detection. This direction is typically in the same direction as the final forging operation.

As with most nondestructive testing modalities, ultrasonic testing has intrinsic limitations that may limit its ability to detect defects under certain conditions. This is particularly the case near boundaries of a forging where a small reflection of sound energy from a defect in the component cannot be resolved from much larger internal reflections of sound energy reflected from the walls of the machined component being examined. In addition, directly under the surface being tested is a volume of material, typically referred to as the transducer dead zone, where defects cannot be detected due to the large interface reflection at the part surface, geometric limitations of the probe or the recovery time associated with the initial pulse of the transducer or instrumentation protection circuitry. The transducer dead zone is also commonly referred to as the initial pulse length.

To achieve improved ultrasonic testing coverage of a finished machined component, the present invention applies a method for modifying a finished machine component forging for ultrasonic inspection. A forging envelope may be constructed in the shape of a right circular cylinder that surrounds a machine component forging. Then material may be added to the forging envelope in the direction of the forging equal to about 2 times a wavelength of an ultrasonic inspection device. Additional material may then be added to an inspection surface of the forging envelope equal to the dimension of a transducer dead zone, if the forging cannot be inspected ultrasonically from two opposing surfaces in the forged direction. Lastly, material may be added to the forging envelope in a direction perpendicular to the forging direction equal to a transducer footprint plus the break edge radius.

DETAILED DESCRIPTION

Figure 1:
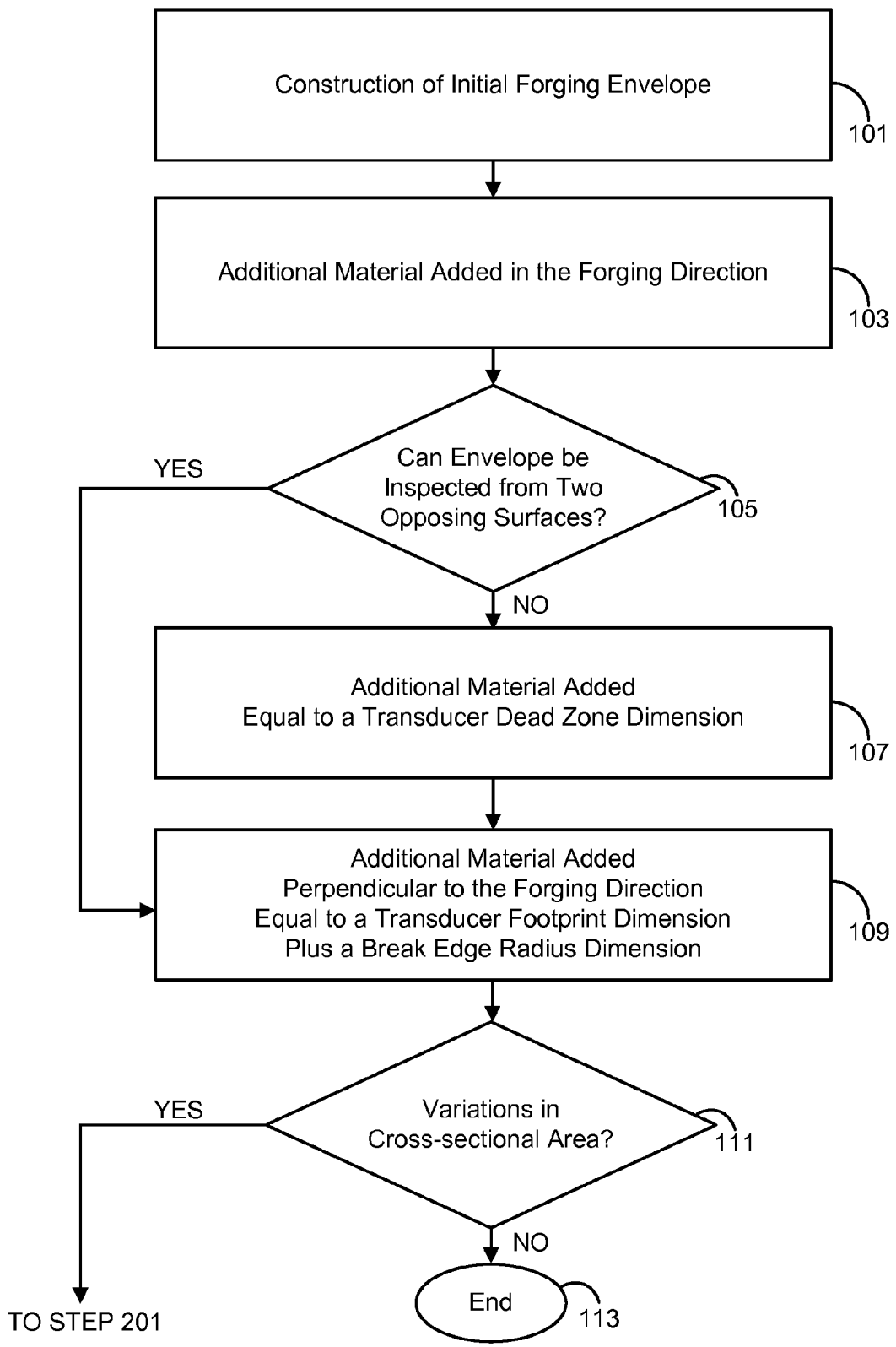
FIG. 1 depicts a process to improve ultrasonic testing coverage in accordance with an embodiment of the present invention.

The present invention now will be described more fully hereinafter with reference to the accompanying drawings, in which some, but not all embodiments of the invention are shown. Indeed, these inventions may be embodied in many different forms and not be construed as limited to the embodiments set forth herein; rather, these embodiments are provided so that this disclosure will satisfy applicable legal requirements. Like numbers refer to like elements throughout.

The present invention is described below with reference to block diagrams and flowchart illustrations of systems, methods, apparatuses and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, CAD systems or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

In an embodiment of the present invention, to improve the shape of the forging envelope for lower weight and improved ultrasonic coverage of the finished machine part, the diameter of the forging is changed to match the finished machine shape where practical. A change in the diameter of the forging is called a step. The forging envelope should be designed to ensure that steps are positioned so that the large reflection from the back wall of the forging doesn't extend into the finished machine part which could effectively mask a reflection from a defect.

One advantage of the present invention over prior art methods and systems is that this process may be easily automated. The advantages inherent in automating the process of the present invention include the reduced chance of human error which may cause certain areas of the forging to not receive adequate ultrasonic inspection coverage and may not result in the lightest weight forging. Furthermore, the design rules applied in the present invention are based on easily measurable parameters of the ultrasonic test system.

The present invention considers a method whereby a forging envelope is created by applying a sequential set of design rules. The design rules are applied to the desired finished machined component shape. It should be understood that this method may be easily programmed using known CAD software packages.

The present invention is based on several factors related to the forging process, forging shape and other applicable ultrasonic testing parameters. First, it is assumed that the direction of ultrasonic sound propagation is based on the forging direction. To remain perpendicular to the forging flow lines, the direction of sound from a transducer must be in the same direction as the materials were forged. For disc shaped forgings, this direction is axial.

Second, there are four applicable parameters associated with the ultrasonic testing that must be factored into the design rules. These are referred to herein as the transducer dead zone, ultrasonic wavelength, ultrasonic beam width and transducer footprint.

The transducer dead zone parameter is determined by the depth of metal obscured by the initial pulse during ultrasonic testing. Once the ultrasonic testing instrument is calibrated for test distance and scanning sensitivity, the initial pulse length is the depth where the amplitude of the trailing edge of the initial pulse decreases to the higher of ten percent of the full screen height or the amplitude of the acoustic noise level of the material.

The ultrasonic wavelength parameter represents the wavelength of the ultrasonic wave produced by the ultrasonic transducer measured using the velocity of sound within the forging and either of the center or peak frequency of the ultrasonic wave. This determination is represented as ultrasonic wavelength=sound velocity/wave frequency.

Likewise, the ultrasonic beam width represents the lateral dimension of the ultrasonic beam as measured from the center line of the transducer to the effective edge of the beam. In the preferred embodiment of the present invention, the effective edge of the beam should be measured using a step block. If this measurement is not or cannot be made, as a general rule, the value of this parameter may be approximated by calculating the result of two times the beam width measured to the first minimum of the sound pressure field. For circular transducers this value is equal to [(2.44*ultrasonic wavelength)/diameter of the transducer]*sound path distance. The sound path distance is defined to be the minimum axial dimension between the step and the opposite inspection surface.

The transducer footprint corresponds to the distance measured from the center of the transducer to its edge. If the transducer is contained in a holder, then the distance is measured from the center of the transducer to the holder.

To achieve improved ultrasonic testing coverage of the finished machined component, the present invention applies a sequential set of design rules using the above parameters to the finished machined shape to produce an improved forging shape with lower weight and which allows for improved test coverage in the forging direction.

In one embodiment of the present invention, the process begins with the final machined component shape. From this shape, a set of three rule categories are applied in sequential order. These can be referred to as cover stock rules, boundary rules and step rules. Cover stock rules are rules that are applicable in the forge or test direction. Boundary rules are rules that are applicable lateral to the forge or test direction. Step rules are rules that are applicable at the forging steps.

Cover stock rules use the ultrasonic test parameters of the transducer dead zone and wavelength to ensure improved ultrasonic inspection coverage in the forged direction of the forging. This direction of the forging is also known as the test direction. Beginning with the final shape, an envelope is constructed in the shape of a right circular cylinder that surrounds the final machined part shape with extra material added in the test direction equal to two times the ultrasonic wavelength. This allows for resolution of defects near the wall opposite from the transducer position.

If the forging can be inspected from two opposing surfaces in the test direction, and the forging thickness is more than twice the transducer dead zone, then no additional material needs to be applied to satisfy the requirements of the cover stock rules. If either of the two requirements is not met, additional material must be added on the inspection surface equal to the dead zone dimension.

In one embodiment of the present invention, after application of the cover stock rules, the boundary rule is applied. The boundary rule uses the transducer footprint to ensure improved ultrasonic inspection coverage lateral to the test direction. Continuing from the shape that was created from the cover stock rules, additional material may be added in the direction perpendicular to the test direction. The amount of extra material added is equal to the transducer footprint added to the end radius of the forging. The end radius is commonly referred to by those skilled in the art as the break edge radius.

In one embodiment of the present invention, subsequent to the application of the boundary rule, the step rules are applied. The step rules are applicable when the finished machined shape has variation in cross sectional area such that changes in the forging envelope can be made by introducing steps into the forging. As discussed above, a step refers to a change in the diameter of the forging. The step rules are only applicable for forgings forged and tested in the axial direction, such as disc shaped forgings. Such forgings are commonly used in the manufacture of land based gas turbines and aircraft engines. The material typically used for such forgings may include, but are not limited to Alloy 706, Alloy 718, CrMoV, NiCrMoV and %12 Cr stainless steel.

Application of the step rules involves three distinct rules. The first of these rules to apply is the side-to-side offset rule. Application of this rule requires that the radial position where a step can be located be based on the geometry of the opposite side of the forging. Unless the forgings are inspected from opposing directions, any step will preclude improved ultrasonic inspection of the final part. When the forging is inspected in opposing directions, steps cannot be positioned at the same radial location on both sides of the forgings because there would be missed inspection coverage at this transition where the transducer cannot be placed on the forging surface due to the step.

To avoid this problem, in one embodiment of the present invention the steps are offset side-by-side radially by the dimension calculated as at or about: Offset=(2*Transducer footprint)−Transition radius+Break edge radius. In the above equation, the transition radius is equal to the machined radius between step surfaces.

It is recognized that a step interferes with the inspection from one surface, even though the bulk of the forging is inspected from the opposing side, as the material located in the transducer dead zone from that side will not be inspected. Therefore, a second rule is subsequently applied that ensures the finished machined part will not lie within a region opposite the step of the below described axial and radial dimensions. The axial dimension is equal to the transducer dead zone. The radial dimension is determined as at or about: (2*transducer footprint)+transition radius+break edge radius.

Finally, a third step rule may be applied in certain embodiments of the present invention. The introduction of a step in the forging envelope may create a back wall echo that can extend into the final part shape due to the beam width of the transducer. To ensure that the back wall echo does not interfere with detections of defects near the step, the finished machined part must not lie within the ultrasonic beam width of the transducer used to inspect from the opposite side of the forging. This rule generally does not apply if the axial dimension of the step transition is greater than the transducer dead zone.

FIG. 1 depicts the operation of one embodiment of the present invention. The method commences at step 101 wherein a forging envelope is constructed in the shape of a right circular cylinder that surrounds the finished machine component. The method next proceeds to step 103 wherein additional material is added to the forging envelope in the forging direction. The amount of additional material added in the forging direction is about equal to 2*the wavelength of the ultrasonic inspection device.

After the completion of step 103, the method proceeds to step 105. At step 105 it is determined whether the forging envelope can be ultrasonically inspected from two opposing surfaces in the forging direction. If it is determined that the forging envelope may be ultrasonically inspected from two opposing surfaces in the forging direction, the method proceeds to step 109. If it is determined that the forging envelope may not be ultrasonically inspected from two opposing surfaces in the forging direction, the method proceeds to step 107. At step 107 additional material is added to the inspection surface of the forging envelope. The amount of additional material added at step 107 is equal to the dimension of the transducer dead zone. After completion of step 107, the method proceeds to step 109.

At step 109, another application of additional material is performed on the forging envelope. The material is added in the direction perpendicular to the forging direction. The amount of material added is equal to the transducer footprint plus the break edge radius. Subsequently, the method proceeds to step 111. At step 111, a determination is made as to whether the finished machine shape has variation in cross-sectional area such that changes in the forging envelope can be made by introducing steps into the forging. Typically, this determination will come out affirmative only for forgings forged and tested in the axial direction, such as disc shaped forgings commonly used in land based gas turbines and aircraft engines.

Figure 2:
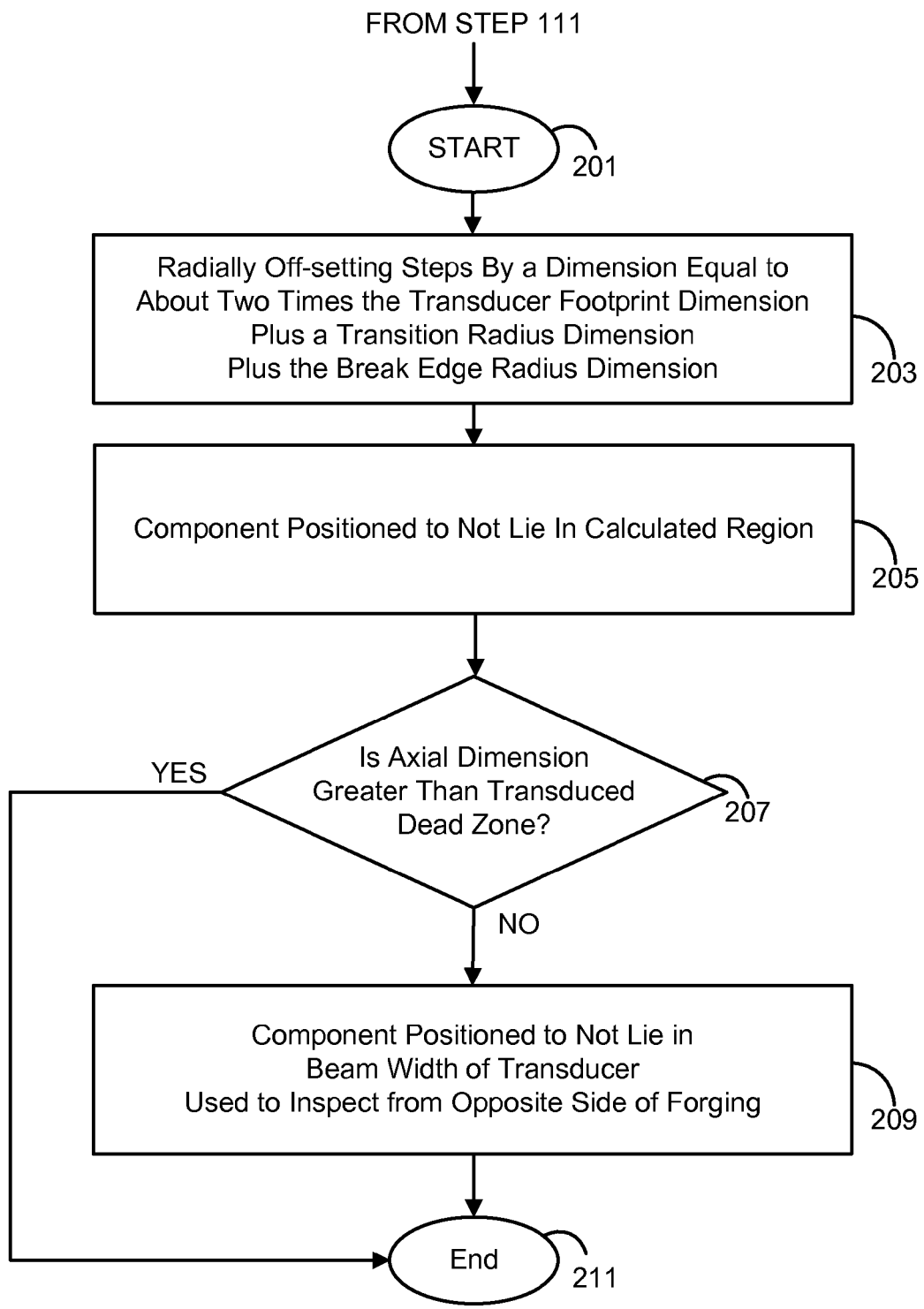
FIG. 2 depicts a second process to improve ultrasonic testing coverage in accordance with an embodiment of the present invention.

If at step 111 it is determined that the finished machine shape has variation in cross-sectional area such that changes in the forging envelope can be made by introducing steps into the forging, the method proceeds to step 201 which is depicted in FIG. 2 and discussed below. If at step 111, it is determined that the finished machine shape does not have variation in cross-sectional area such that changes in the forging envelope can be made by introducing steps into the forging, the method terminates at step 113.

FIG. 2 depicts the method of operation of an embodiment of the present invention. The method begins at step 201 which point is reached based on an affirmative determination being made in step 113 as described above. The method next proceeds to step 203 where the steps are radially offset in the forging envelope by a dimension about equal to 2*transducer footprint+transition radius+break edge radius. The transition radius is the machined radius between step surfaces.

Subsequently, the method proceeds to step 205, where the finished machine component is positioned such that it does not lie within a region opposite the step with an axial dimension equal to the transducer dead zone and a radial dimension about equal to 2*transducer footprint+transition radius+break edge radius. The transition radius is the machined radius between step surfaces.

Next, the method proceeds to step 207, wherein a determination is made as to whether the axial dimension of the step transition is greater than the transducer dead zone. If it is determined that the axial dimension of the step transition is greater than the transducer dead zone the method proceeds to step 211 and concludes. However, if at step 207 it is determined that the axial dimension of the step transition is not greater than the transducer dead zone, the method proceeds to step 209.

At step 209, the finished machine component is positioned such that the component does not lie within the ultrasonic beam width of the transducer used to inspect from the opposite side of the forging. Subsequently, the method concludes at step 211.

Figure 3:
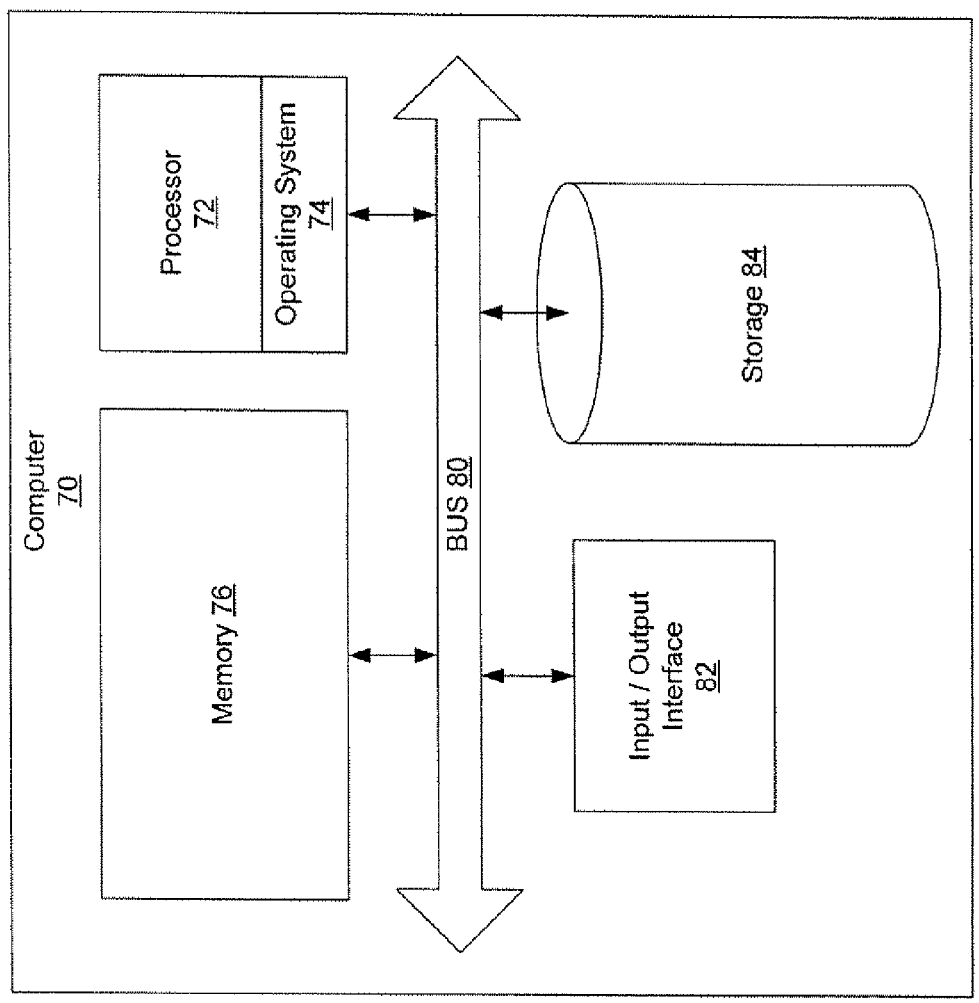
FIG. 3 depicts a block diagram of a computer capable of operating according to one aspect of the present invention.

It will be appreciated that each of the methods described above with respect to FIGS. 1 and 2 may be implemented by computer software and/or hardware, as described next with reference to FIG. 3. FIG. 3 shows a block diagram of a computer 70, according to one aspect of the present invention. The computer 70 generally includes a processor 72, operating system 74, memory 76, input/output (I/O) interface 82, storage 84 and bus 80. The bus 80 includes data and address bus lines to facilitate communication between the processor 72, operating system 74 and the other components within the module 70, including the memory 76, the input/output (I/O) interface 82 and the storage 84. The processor 72 executes the operating system 74, and together the processor 72 and operating system 74 are operable to execute functions implemented by the computer 70, including software applications stored in the memory 76, as is well known in the art. Specifically, to implement the methods described herein with respect to FIGS. 1 and 2, the processor 72 and operating system 74 are operable with the I/O interface 82 to obtain input values provided by an operator of the system. According to one aspect of the invention, memory 76 may include one or more algorithms for executing the methods and processes described above with respect to FIGS. 1 and 2.

It will be appreciated that the memory 76 may include random access memory, read-only memory, a hard disk drive, a floppy disk drive, a CD-Rom drive, or optical disk drive, for storing information on various computer-readable media, such as a hard disk, a removable magnetic disk, or a CD-ROM disk. Generally, the memory 76 receives information input or received by the computer 70, including the various parameters used in application of the rules described in embodiments of the present invention through an I/O interface 82. Using information it receives, the memory 76 effects the methods described in detail above with respect to FIGS. 1 and 2 to calculate the correct parameters for a forging envelope which will allow for improved ultrasonic inspection coverage of the completed machined part. Therefore, the memory 76 may be operable to execute computations of parameters, compare the parameters against criteria, process information, and the like, as needed to execute the methods described herein.

The storage 84 of the computer 70, which is connected to the bus 80 by an appropriate interface, may include random access memory, read-only memory, a hard disk drive, a floppy disk drive, a CD-Rom drive, or optical disk drive, for storing information on various computer-readable media, such as a hard disk, a removable magnetic disk, or a CD-ROM disk. In general, the purpose of the storage 84 is to provide non-volatile storage to the computer 70. The storage may include one or more criteria against which the calculated parameters may be compared against.

It is important to note that the computer-readable media described above with respect to the memory 76 and storage 84 could be replaced by any other type of computer-readable media known in the art. Such media include, for example, magnetic cassettes, flash memory cards, digital video disks, and Bernoulli cartridges. It will also be appreciated by one of ordinary skill in the art that one or more of the computer 70 components may be located geographically remotely from other computer 70 components.

It should also be appreciated that the components illustrated in FIG. 3 support combinations of means for performing the specified functions described herein. As noted above, it will also be understood that each of the methods described above, including the processes and computations described with reference to FIGS. 1 and 2, can be implemented by special purpose hardware-based computer systems that perform the specified functions or steps, or combinations of special purpose hardware and computer instructions. For example, in one embodiment of the present invention, the methods described may be applied through a CAD computer system. Further, the computer 70 may be embodied as a data processing system or a computer program product on a computer-readable storage medium having computer-readable program code means embodied in the storage medium. Any suitable computer-readable storage medium may be utilized including hard disks, CD-ROMs, DVDs, optical storage devices, or magnetic storage devices. Additionally, although illustrated individually in FIG. 3, each component of the computer 70 may be combined with other components within the computer 70 to effect the functions described herein. Accordingly, the computer 70 may take the form of an entirely hardware embodiment, an entirely software embodiment or an embodiment combining software and hardware aspects, such as firmware.

Figure 4:
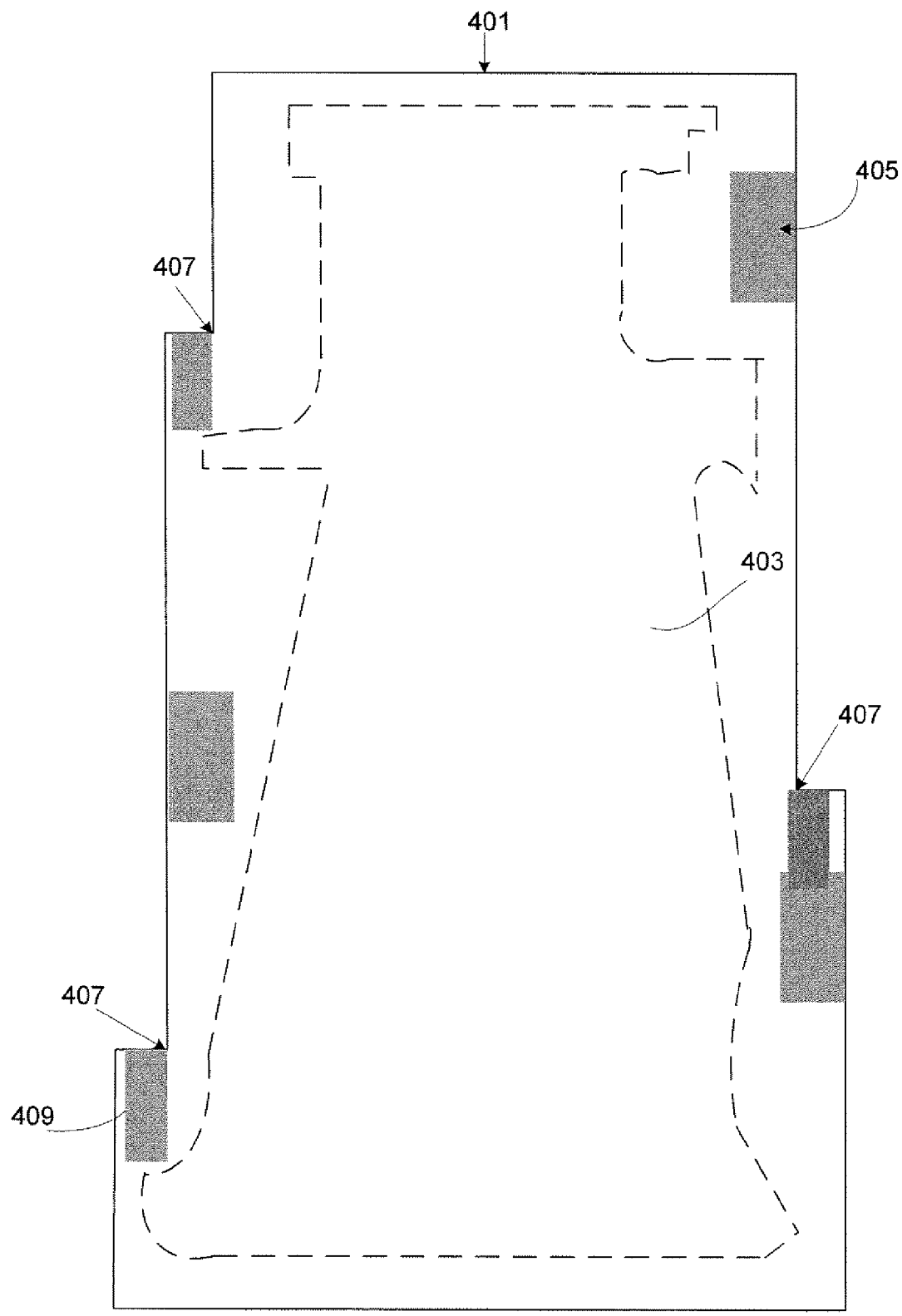
FIG. 4 depicts an illustration of a forging envelope according to an embodiment of the present invention.

FIG. 4 depicts an illustration of a forging envelope 401 according to an embodiment of the present invention. The envelope 401 started with the finished machined part shape 403 and includes a number of steps 407. In this particular illustration, it is ensured that the finished machine component 403 does not lie within a region 405 opposite the step 407 with an axial dimension equal to the transducer dead zone and a radial dimension equal to two times the transducer footprint plus the transition radius plus the break edge radius, where the transition radius is the machined radius between step surfaces.

Furthermore, if the axial dimension of the step transition is not greater than the transducer dead zone, it is ensured that the finished machine component 403 does not lie within a region 409 consisting of the ultrasonic beam width of a transducer used to inspect from the opposite side of the forging 401. In this illustration, it is assumed that the axial dimension of the step transition is not greater than the transducer dead zone.

Many modifications and other embodiments of the inventions set forth herein will come to mind to one skilled in the art to which these inventions pertain having the benefit of the teachings presented in the foregoing descriptions and the associated attachments. Therefore, it is to be understood that the inventions are not to be limited to the specific embodiments disclosed and that modifications and other embodiments are intended to be included within the scope of the present disclosure. Although specific terms are employed herein, they are used in a generic and descriptive sense only and not for purposes of limitation.

We claim:

1. A method for modifying a finished machine component forging for ultrasonic inspection, the method comprising the steps of:
    constructing a forging envelope in the shape of a right circular cylinder that surrounds a machine component forging;
    adding material to the forging envelope in the direction of the forging equal to about 2 times a wavelength of an ultrasonic inspection device;
    adding additional material to an inspection surface of the forging envelope equal to a transducer dead zone dimension, if the forging cannot be inspected ultrasonically from two opposing surfaces in the forged direction; and
    adding additional material to the forging envelope in a direction perpendicular to the forging direction equal to a transducer footprint dimension a break edge radius dimension.

2. The method of claim 1, further comprising the steps of:
    radially offsetting steps in the forging envelope by a dimension equal to about two times the transducer footprint dimension plus a transition radius dimension plus the break edge radius dimension, where the transition radius dimension is a dimension of a machined radius between step surfaces;
    determining that the finished machine component does not lie within a region opposite the step with an axial dimension equal to the transducer dead zone dimension and a radial dimension equal to two times the transducer footprint dimension plus the transition radius dimension plus the break edge radius dimension;
    if the axial dimension of the step transition is not greater than the transducer dead zone dimension, ensuring that the finished machine component does not lie within an ultrasonic beam width of a transducer used to inspect from the opposite side of the forging.

3. The method of claim 2, wherein the finished machine component forging has variation in cross-sectional area such that changes in the forging envelope can be made by introducing steps into the forging.

4. The method of claim 3, wherein the forging is forged and tested in the axial direction.

5. The method of claim 3, wherein the forging is a disc-shaped forging.

* * * * *